United States Patent [19]
Wei et al.

[11] Patent Number: 5,778,906
[45] Date of Patent: *Jul. 14, 1998

[54] DENTAL FLOSS HOLDER

[76] Inventors: Kuang-Hsing Wei; Kuang-Hung Wei, both of 18500 Bay Leaf Way, Germantown, Md. 20874

[*] Notice: The term of this patent shall not extend beyond the expiration date of Pat. No. 5,570,710.

[21] Appl. No.: 713,810

[22] Filed: Sep. 13, 1996

Related U.S. Application Data

[63] Continuation-in-part of Ser. No. 528,889, Sep. 15, 1995, Pat. No. 5,570,710, Ser. No. 581,372, Dec. 29, 1995, Pat. No. 5,653,246, and Ser. No. 698,734, Aug. 16, 1996.
[51] Int. Cl.⁶ ............................................ A61C 15/00
[52] U.S. Cl. ........................................ 132/327; 132/323
[58] Field of Search ............................ 132/321, 323, 132/324, 326, 327, 328, 329

[56] References Cited

U.S. PATENT DOCUMENTS

| | | | |
|---|---|---|---|
| 2,644,469 | 7/1953 | Cohen | 132/321 |
| 4,050,470 | 9/1977 | Miller | 132/323 |
| 4,403,625 | 9/1983 | Sanders et al. | 132/321 |
| 4,638,824 | 1/1987 | De La Hoz | 132/323 |
| 5,503,168 | 4/1996 | Wang | 132/321 |

*Primary Examiner*—Gene Mancene
*Assistant Examiner*—Pedro Philogene

[57] ABSTRACT

A dental floss holder for securely fastening one end of a dental floss instead of winding it around a finger includes a first member, at least one pair of matching surfaces, a second member, and threaded surface or a frustum surface and a uniform surface for locking the first and second members together. One of the matching surfaces is formed on the first member and the other on the second member. When the first and second members lock together, the dental floss is securely fastened between at least one pair of the matching surfaces. Also, at least one notch is provided for facilitating the retention of the floss.

34 Claims, 2 Drawing Sheets

(left)  (right)

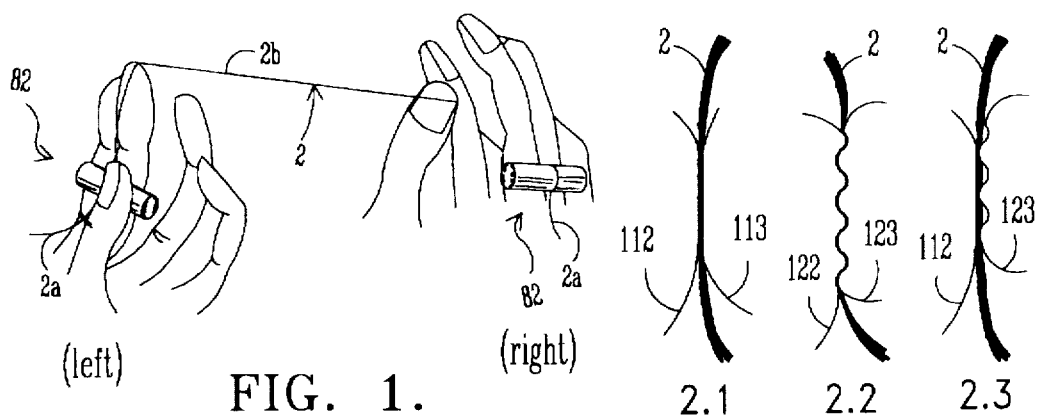
FIG. 1.
FIG. 2.
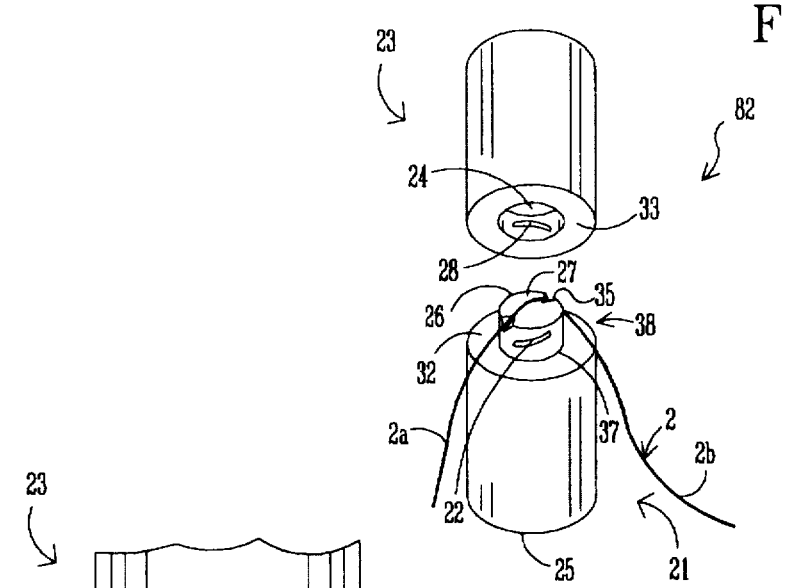
FIG. 3.
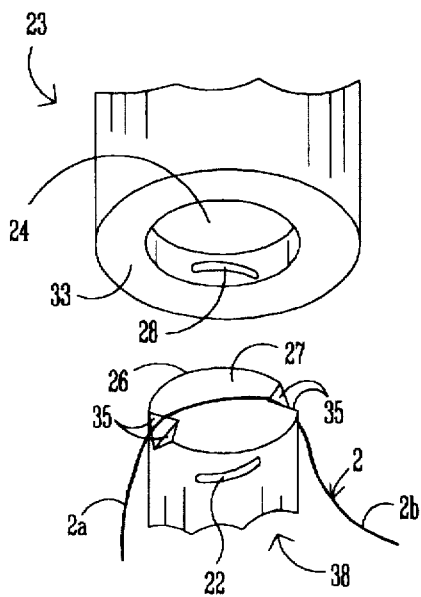
FIG. 4.
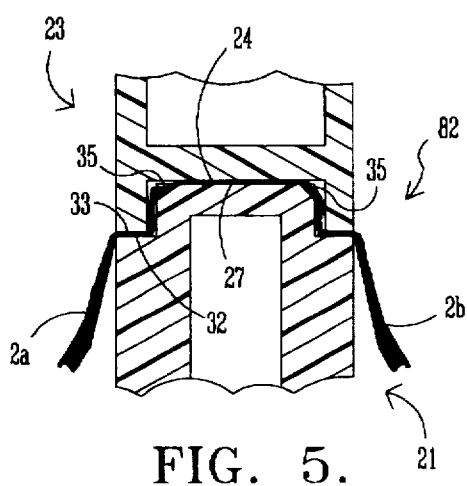
FIG. 5.

DENTAL FLOSS HOLDER

This is a CIP of application Ser. No. 08/528889 filed Sep. 15, 1995, U.S. Pat. No. 5,570,710 and a CIP of application Ser. No. 08/581372 filed Dec. 29, 1995, U.S. Pat. No. 5,653,246 and a CIP Ser. No. 698,734 filed Aug. 16, 1996 now pending.

BACKGROUND OF THE INVENTION

Part 1. The Field of the Invention

This invention relates to the teeth cleaning with a length of dental floss and provides as its general object an improved device which is used to securely fasten dental floss and to render teeth-cleaning more effectively.

Part 2. Description of the Prior Art

There are many devices attempting to render flossing less tedious and make it more effective and convenient. Moreover, a growing number of dentists and orthodontists recommend highly for cleaning teeth daily by using dental floss to remove food particles between teeth. However, most people still don't floss daily, even those who take teeth-cleaning and dental care seriously. The inconvenience and discomfort for maneuvering the dental floss by winding ends of a length of dental floss around two fingers is the main reason. The winding ends of a length of dental floss around two fingers will not only cause discomfort on fingers but also render difficulties in manipulating in mouth. Although there are numerous devices with a predetermined length of floss fixed in a two-pronged dental device, maneuvering with two fingers winding a length of dental floss is still the most effective way of daily dental floss cleaning, especially for reaching and positioning between the rear most teeth, and is highly recommended by the dental professions. U.S. Pat. No. 4,050,470 to Miller (1977) provides a dental floss holder with an inwardly tapered slot extending along one elongate edge which does not fasten the dental floss securely in place to facilitate the manipulating of the floss in mouth. U.S. Pat. No. 4,638,824 to De La Hoz (1987) provides a pair of dental floss finger rings having three cut out prongs for retaining a length of dental floss. The retaining prongs are prone to cut the floss at the retaining point as a result of strong force applied during flossing. Also, the floss tends to be pull out of the prongs during flossing operation which requires different angles for inserting floss between teeth at different positions.

SUMMARY OF THE INVENTION

It is a general object of the invention to provide a dental floss holder and a method for fastening one end of a dental floss. A dental floss holder for securely fastening one end of a dental floss instead of winding it around a finger includes a first member, at least one pair of matching or corresponding surfaces, a second member, and locking means. One of the matching surfaces is formed on the first member and the other matching surface on the second member. When the first and second members lock together, the dental floss is securely fastened between at least one pair of the matching surfaces. Also, the first member may comprise at least one notch to facilitate the retention of the floss.

The method of fastening one end of a dental floss includes first placing or retaining the dental floss on the first member. It then follows with locking the second member with the first member so as to lock at least one pair of the matching surfaces together to securely fasten the dental floss therebetween.

Accordingly, several objects and advantages of the present invention are:

(a) to provide an improved dental floss holder which is used to eliminate the discomfort caused by winding a length of dental floss around fingers;

(b) to provide an improved dental floss holder which is designed to save the wasteful of floss for winding an extra length of dental floss around fingers;

(c) to provide an improved dental floss holder for securely fastening dental floss ends than winding around fingers, which is needed to be rewound several times during the course of teeth-cleaning; and (d) to provide an improved dental floss holder to better control of a strained floss and perform a more effective teeth-cleaning.

Further objects and advantages of the invention will become apparent from the appended drawings and the ensuing specifications.

DRAWING FIGURES

FIG. 1 is a perspective view showing the use of the dental floss holders with a dental floss fastened in each holder;

FIG. 2 illustrates the inventive concept of the invention;

FIG. 3 is a perspective view of the dental floss holder with the first member being separated from the second member;

FIG. 4 is a fragmentary perspective view showing details of the dental floss holder of FIG. 3, taken on an enlarged scale for clarity;

FIG. 5 is a fragmentary sectional view showing details of a portion of the dental floss fastened in the dental floss holder of FIG. 3 in a locked position, taken on an enlarged scale for clarity;

DETAILED DESCRIPTION OF THE PREFERRED EMBODIMENT

Figure 6:
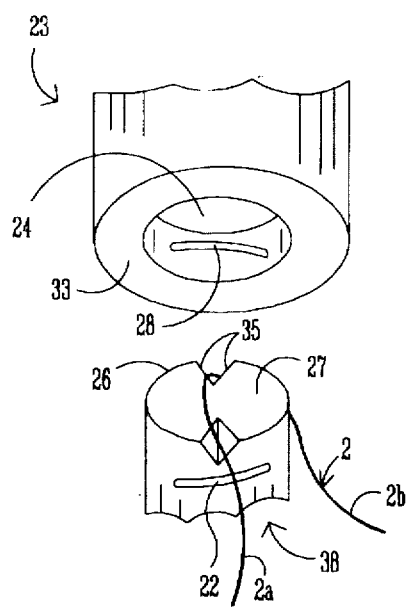
FIG. 6 is a perspective view of another working example similar to FIG. 4.

Referring to FIG. 1, it illustrates that a length of conventional dental floss 2 connects two identical dental floss holders 82. The dental floss 2 includes a middle section 2b and two end sections 2a. Each end section 2a defines each end portion of the floss 2 extending out from the dental floss holder 82. The middle section 2b defines the portion of the floss 2 between the holders 82 and connects both the holders 82. Each dental floss holder 82 is easily manipulated by each hand so that the floss 2 is ready to be used inside mouth to clean teeth (not shown) as one usually does with both ends of a dental floss winding around fingers. One of the dental floss holders 82 may be held inside one hand (left of FIG. 1), and the other holder may be supported by the back of the other hand (right of FIG. 1) to clean teeth. The dental floss holders 82 provide much better control of the floss 2 and eliminate the discomfort by winding ends of a dental floss around fingers. A single holder may be used on one hand with the opposite end of the dental floss fastened by some other means or by fingers; however, it is expected that two holders will be used. The dental floss holder 82 is suitable for use with the conventional thread or cord type of dental floss or with ribbon or band type of floss. It should be understood that the term "dental floss" is used generically to indicate any type of floss.

The concept of this invention for securely fastening one end of the floss 2 between a pair of matching or corresponding or mating surfaces is best shown in FIG. 2. In 2.1 of FIG. 2, the floss 2 is securely fastened between a surface 112 and a surface 113. The surfaces 112 and 113 are configured to have matching dimensions such that when both the surfaces 112 and 113 join together or abut against each other closely by locking means, the cross-sectional dimension of the floss 2 is compressed between the surfaces 112 and 113 so that the floss 2 is securely fastened therebetween. In 2.2 of FIG. 2, a surface 122 and a surface 123 provide the same fastening function, except that the surfaces 122 and 123 comprise the form of matching threaded or screw surfaces, or small ridges, or corrugated surfaces. Also, in 2.3 of FIG. 2, the surface 112 and the surface 123 may be designed to provide the same fastening function.

Referring to FIGS. 3, 4 and 5, each dental floss holder 82 comprises a first member 21 which preferably comprises a generally elongated cylindrical piece of material dimensioned to be easily handled by fingers for retaining the floss 2 on the first member 21. The first member 21 has a first end 26, a second end 25, a third end 37, and an upper portion 38. The first end 26 and the second end 25 are on either end of the first member 21. The first end 26 and the third end 37 are on either end of the upper portion 38. The upper portion 38 has a first outer surface 27 which is preferably integrally formed at the first end 26. The upper portion 38 also has two notches 35 formed substantially on either side at the first end 26 to facilitate the retention of the floss 2 on the first member 21. However, having only one of the notches 35 on only one side of the upper portion 38 still serves the purpose. The notch 35 defines a generally V-shaped angular cut or opening formed substantially at the circumference of the first outer surface 27. The notch 35 cuts a small corner of the upper portion 38 substantially at the first end 26. The depth of the notch 35 cutting into the upper portion 38 is preferably about one-sixth the diameter of the first outer surface 27. The angle of the notch 35 is preferably between about 35° and 120°. However, the size and the angle of the notch 35 may be selected outside the preferred range as required. The upper portion 38 also has a plurality of spaced thread segments 22. Each thread segment 22 has the same pitch, starts at the same height, and ends at the same lower height on the upper portion 38. In this example, it provides two equally spaced external thread segments 22, each extending about 75°–90° substantially on the opposite side of the outer circumference of the upper portion 38. However, the number of thread segments can be selected as required and the angular extent can be obtained accordingly. The first member 21 also has a second outer surface 32 which defines a surface having a circumference larger than that of the first outer surface 27. The second outer surface 32 connects with the upper portion 38 at the third end 37.

Referring still to FIGS. 3, 4 and 5, each dental floss holder 82 comprises a second member 23. The second member 23 comprises preferably a generally elongated cylindrical piece of material and is also dimensioned to be easily handled by fingers. The second member 23 comprises internal thread segments 28 that are dimensioned to rotate freely relative to the external thread segments 22. The second member 23 comprises a third outer surface 33 to match with the second outer surface 32 of the first member 21. The third outer surface 33 defines a rim surface formed on the second member 23. The second member 23 also comprises an inner surface 24 that is the matching surface of the first outer surface 27. The inner surface 24 defines an inner end surface formed on the second member 23. When the first and second members 21 and 23 screw together with each other, the first outer and inner surfaces 27 and 24 as well as the second and third surfaces 32 and 33 abut against each other closely. Therefore, the floss 2 is securely fastened therebetween. As shown in FIG. 5, the cross-sectional dimension of the floss 2 is compressed between the surfaces 27 and 24 as well as the surfaces 32 and 33 when the first and second members 21 and 23 lock together. Therefore, the closely abutted surfaces 27 and 24 as well as the surfaces 32 and 33 are to effectively fasten the compressed dental floss 2 therebetween. However, when the floss 2 is fastened between only one pair of the surfaces 27 and 24, and the surfaces 32 and 33, either pair of the matching surfaces alone is sufficient enough to fasten the floss 2. Also, the form of the matching surfaces may be designed like 2.1, 2.2, and 2.3 of FIG. 2 as required.

The dental floss holder 82 of FIG. 6 is similar to that of FIGS. 3, 4 and 5, except that the thread segments 22 are designed substantially beneath the notches 35 on substantially the same side of the first member 21 so that when the floss 2 is retained across the notches 35, the floss 2 is also retained across the thread segments 22, as shown in FIG. 6. Still, the thread segments 28 are dimensioned to screw together with the thread segments 22. When the first and second members 21 and 23 screw together with each other, the floss 2 also engages with the thread segments 22 and 28. As a result, the floss 2 is also fastened between the thread segments 22 and 28. Therefore, the floss 2 is fastened between the first outer and the inner surfaces 27 and 24, the second and the third surfaces 32 and 33, and the thread segments 22 and 28. However, any one pair of the above engagement alone can be dimensioned to fasten the floss 2. It is understood that the floss 2 in FIG. 4 may also be retained across the thread segments 22 so that the floss 2 may engage with the thread segments 22 and 28 when the first and second members 21 and 23 screw together with each other. When the floss 2 is retained across the thread segments 22 in FIG. 4, the floss 2 may not cross the notches 35, which will not affect the fastening engagement between the floss 2 and the thread segments 22 and 28.

Figure 7:
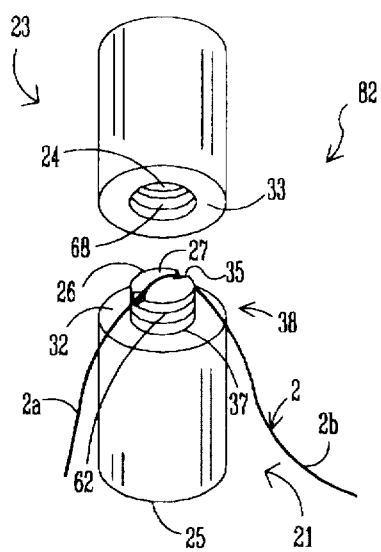
FIG. 7 is a perspective view of another working example similar to FIG. 3.

The dental floss holder 82 of FIG. 7 is similar to that of FIGS. 3, 4, 5 and 6, except that the thread segments 22 and 28 are in the form of a threaded surface 62 and a matching threaded surface 68. The threaded surfaces 62 and 68 are free to rotate relative to each other. The threaded surfaces 62 and 68 are dimensioned such that the floss 2 is also securely fastened between the threaded surfaces 62 and 68 when the first and second members 21 and 23 screw together with each other. Therefore, the floss 2 is fastened between the surfaces 27 and 24. However, the surfaces 32 and 33, and the surfaces 62 and 68 may also be dimensioned to fasten the floss 2. It is understood that the term "threaded surface" is used generically to indicate any threaded configurations that can be threadably engageable with each other. Therefore, the threaded surfaces 62 and 68 generically include the thread segments 22 and 28. Otherwise, the holder 82 in FIG. 7 is identical to that in FIG. 3 or 6 in operation, in resultant effects, and generally in structure. The length of the engagement between the floss 2 and the matching surfaces can be designed according to the shapes or forms, the number of pairs of matching surfaces, and the physical locations of the matching surfaces related to each other. It is understood that any one pair of the matching surfaces alone can be dimensioned to securely fasten the floss 2.

Figure 8:
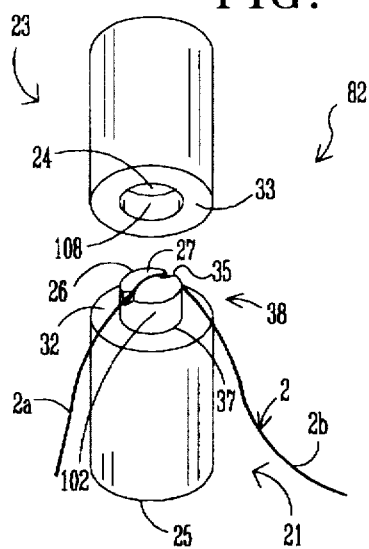
FIG. 8 is a perspective view of another working example similar to FIG. 3.
Figure 9:
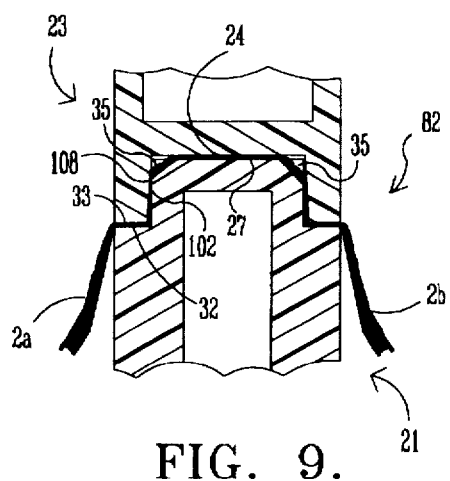
FIG. 9 is a fragmentary sectional view showing details of a portion of the dental floss fastened in the dental floss holder of FIG. 8 in a locked position, taken on an enlarged scale for clarity.

The dental floss holder 82 of FIGS. 8 and 9 is similar to that of FIG. 7, except that the threaded surfaces 62 and 68 are replaced by an outer uniform surface 102 and an inner frustum surface 108. The outer uniform surface 102 is preferably integrally formed substantially on the external peripheral surface of the upper portion 38. The outer uniform surface 102 has a diameter substantially uniform throughout its outer length. The surface 108 preferably comprises generally the form of a frustum or conical configuration. The surface 108 has a larger diameter end and a smaller diameter end. The larger diameter end of the surface 108 connects with the third outer surface 33, and the smaller diameter end connects with the inner surface 24. The diameter of the surface 102 is dimensioned to be slightly smaller than the larger diameter of the surface 108, and slightly larger than the smaller diameter of the surface 108.

When the first member 21 engages with the second member 23, the surface 102 inserts into the surface 108 through the larger diameter end at the outer surface 33. As the surface 102 proceeds longitudinally a distance, preferably about one-third the longitudinal length of the surface 108, into the surface 108 where the diameter of the surface 102 is substantially equal to that of the surface 108, the surface 102 contacts with the surface 108. As a result, the insertion movement of the surface 102 is restricted by the surface 108. The surface 108 and/or the surface 102 may comprise any suitable materials having a certain degree of resilience so that the surface 102 can still further proceed toward the inner surface 24 upon applying a force, for example a push and/or a twist from a hand. The surfaces 102 and 108 frictionally abut against each other so closely such that the floss 2 is compressed between the surfaces 102 and 108. Therefore, the floss 2 is securely fastened between the surfaces 102 and 108. However, the surfaces 27 and 24, and/or the surfaces 32 and 33 may also be dimensioned to fasten the floss 2. It is understood that the locking engagement between the outer uniform surface 102 and the inner frustum surface 108 may be dimensioned like the engagement between the two equally spaced thread segments 22 and 28, wherein the engagement between the thread segments 22 and 28 extends about 75°–90° on either side of the first and second members 21 and 23. When the thread segments 22 and 28 lock together with each other, the floss 2 may be placed between the locking engagement of the thread segments 22 and 28 so that the floss 2 is fastened between the thread segments 22 and 28, as shown in FIG. 6. However, when the floss 2 is not placed between the locking engagement of the thread segments 22 and 28, the floss 2 is not fastened between the thread segments 22 and 28, as shown in FIG. 4. When the surfaces 102 and 108 engage with each other on either side of the first and second members 21 and 23, the locking engagement may extend about 75°–90° on either side. Therefore, the floss 2 may not engage with the locking engagement of the surfaces 102 and 108 extending only about 75°–90° on either side of the first and second members 21 and 23. As a result, the floss 2 may not be fastened between the surfaces 102 and 108 when the floss 2 is not placed between the engagement of the surfaces 102 and 108, which extends about 75°–90° on either side of the first and second members 21 and 23. Therefore, the floss 2 is fastened between the surfaces 27 and 24, and/or the surfaces 32 and 33. Therefore, the floss 2 may be fastened between at least one pair of the surfaces 27 and 24, the surfaces 32 and 33, and the surfaces 102 and 108. The threaded surfaces 62 and 68 and the surfaces 102 and 108 may be designed to function as locking means to lock the first and second members 21 and 23 only, or as locking means as well as fastening means to lock and, at the same time, to fasten the floss 2. However, any other locking means, such as a clamp, to clamp the members 21 and 23 together may be used. The surfaces 102 and 108 may also be dimensioned like the surfaces 112 and 123 having the form of corrugated surfaces.

Figure 10:
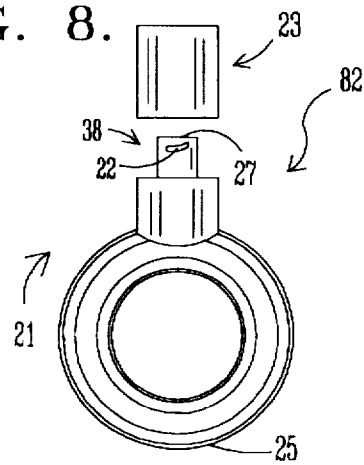
FIG. 10 is a front view of another working example.

The dental floss holder 82 of FIG. 10 is similar to that of FIG. 3, except that the first member 21 comprises substantially the form of a ring which is adapted to fit a finger so that the ring may be inserted into a finger when cleaning teeth. Similarly, the second member 23 may also comprise substantially the form of a ring as required. Otherwise, the holder 82 in FIG. 10 is identical to that in FIG. 3 in operation, in resultant effects, and generally in structure.

The method of fastening one end of the floss 2 according to the invention includes first placing or retaining one end of the floss 2 on the first member 21 at the first end 26 with the end section 2a substantially near the second end 25 along one side of the first member 21 and the middle section 2b along the other side of the first member 21 so that the floss 2 extends from the end section 2a substantially near the second end 25, reaches generally longitudinally to the first end 26 along one side of the first member 21, crosses generally transversely over the first member 21 at the first end 26, and then extends generally longitudinally toward the second end 25 along the other side of the first member 21 to the middle section 2b. The floss 2 may be held by fingers against the first member 21 on both sides to facilitate the retention of the floss 2.

Having the floss 2 retained on the first member 21 with the sections 2a and 2b on both sides of the first member 21, the method continues with the step of engaging or locking the second member 23 with the first member 21 so as to fasten the floss 2 between at least one pair of the following matching surfaces: the inner and first outer surfaces 24 and 27, the second and third outer surfaces 32 and 33, and the surfaces 62 and 68 or the surfaces 102 and 108.

The step of placing may be performed by placing the floss 2 across at least one of the notches 35.

The step of locking is performed by screwing together the thread segments 22 and 28, the threaded surfaces 62 and 68, or the surfaces 102 and 108.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

We claim:

1. A dental floss holder for fastening a dental floss, said holder comprising:

a first member having a surface thereon;

a second member having a matching surface thereon, said matching surfaces being engageable with each other to fasten the floss therebetween; and locking means for locking said first and second members together so that the floss is fastened between said matching surfaces, whereby said holder having the floss fastened therein is manipulated by a hand in lieu of winding the floss around a finger for teeth cleaning.

2. The holder of claim 1, wherein said matching surfaces are selected from the group consisting of:

(a) a second outer surface and a matching third outer surface;

(b) a first outer surface and a matching inner surface;

(c) matching threaded surfaces; and (d) a substantially uniform surface and a matching substantially frustum surface.

3. The holder of claim 1, wherein said locking means comprises a configuration selected from the group consisting of:

(a) matching threaded surfaces;

(b) matching thread segments; and (c) a substantially uniform surface and a matching substantially frustum surface.

4. The holder of claim 1, wherein one of said first and second members further comprises at least a notch defining an angular cut formed substantially at one end thereof.

5. The holder of claim 1, wherein at least one of said first and second members comprises a configuration adapted to be handled by fingers, whereby the floss may be held against both sides of said one member to facilitate the retention of the floss, said configuration selected from the group consisting of:

(a) a substantially ring-shaped configuration adapted to be fitted into a finger;

(b) a substantially cylindrical configuration; and (c) a substantially elongated configuration.

6. A dental floss device for fastening a length of dental floss, said device comprising:

two separate dental floss holders for fastening the floss in a spaced apart relationship, at least one of said holders comprising:

a first member having a surface thereon;

a second member having a matching surface thereon, said matching surfaces being engageable with each other to fasten the floss therebetween; and locking means for locking said first and second members together so that the floss is fastened between said surfaces, whereby each of said holders having the floss fastened therein is manipulated by each hand in a spaced apart relationship for teeth cleaning.

7. The device of claim 6, wherein said matching surfaces of said at least one of said holders are selected from the group consisting of:

(a) a second outer surface and a matching third outer surface;

(b) a first outer surface and a matching inner surface;

(c) matching threaded surfaces; and (d) a substantially uniform surface and a matching substantially frustum surface.

8. The device of claim 6, wherein said locking means of said at least one of said holders comprises a configuration selected from the group consisting of:

(a) matching threaded surfaces;

(b) matching thread segments; and (c) a substantially uniform surface and a matching substantially frustum surface.

9. The device of claim 6, wherein one of said first and second members of said at least one of said holders further comprises at least a notch defining an angular cut formed substantially at one end thereof to facilitate the retention of the floss.

10. The device of claim 6, wherein at least one of said first and second members of said at least one of said holders comprises a configuration adapted to be handled by fingers, said configuration selected from the group consisting of:

(a) a substantially ring-shaped configuration adapted to be fitted into a finger;

(b) a substantially cylindrical configuration; and (c) a substantially elongated configuration.

11. A dental floss holder for fastening a dental floss, said holder comprising:

a first member having a first outer surface formed thereon;

a second member having a matching inner surface formed substantially at an inner end thereof, said inner surface being engageable with said first outer surface to fasten the floss between said surfaces; and locking means for locking said first and second members together so that the floss is fastened between said surfaces, whereby said holder having the floss fastened therein is manipulated by a hand in lieu of winding the floss around a finger for teeth cleaning.

12. The holder of claim 11, wherein said locking means comprises a configuration selected from the group consisting of:

(a) matching threaded surfaces;

(b) matching thread segments; and (c) a substantially uniform surface and a matching substantially frustum surface.

13. The holder of claim 11, wherein one of said first and second members further comprises at least a notch defining an angular cut formed substantially at one end thereof to facilitate the retention of the floss.

14. The holder of claim 11, wherein at least one of said first and second members comprises a configuration adapted to be handled by fingers, whereby the floss may be held against both sides of said one member to facilitate the retention of the floss, said configuration selected from the group consisting of:

(a) a substantially ring-shaped configuration adapted to be fitted into a finger;

(b) a substantially cylindrical configuration; and (c) a substantially elongated configuration.

15. The holder of claim 11, wherein said first outer surface is formed substantially at an outer end of said first member.

16. A dental floss device for fastening a length of dental floss, said device comprising:

two separate dental floss holders for fastening the floss in a spaced apart relationship, at least one of said holders comprising:

a first member;

a second member;

a first outer surface;

an inner surface, said first outer surface formed on one of said first and second members, said inner surface formed substantially at an inner end of the other of said first and second members, said surfaces being engageable with each other to fasten the floss between said surfaces; and locking means for locking said first and second members together so that the floss is fastened between said surfaces, whereby each of said holders having the floss fastened therein is manipulated by each hand in a spaced apart relationship for teeth cleaning.

17. The device of claim 16, wherein said locking means of said at least one of said holders comprises a configuration selected from the group consisting of:

(a) matching threaded surfaces;

(b) matching thread segments; and (c) a substantially uniform surface and a matching substantially frustum surface.

18. The device of claim 16, wherein one of said first and second members of said at least one of said holders further comprises at least a notch defining an angular cut formed substantially at one end thereof to facilitate the retention of the floss.

19. The device of claim 16, wherein at least one of said first and second members of said at least one of said holders comprises a configuration selected from the group consisting of:
   (a) a substantially ring-shaped configuration adapted to be fitted into a finger;
   (b) a substantially cylindrical configuration; and
   (c) a substantially elongated configuration.

20. The device of claim 16, wherein said first outer surface is formed substantially at an outer end of said one member.

21. A method of fastening a dental floss, comprising the steps of:
   placing the floss on one of a first member and a second member, said first member having a surface thereon, said second member having a matching surface thereon, said surfaces being engageable with each other to fasten the floss between said surfaces; and
   locking said first member and said second member together so that the floss is fastened between said surfaces, whereby said first and second members having the floss fastened therein are manipulated by a hand in lieu of winding the floss around a finger for teeth cleaning.

22. The method of claim 21, wherein the locking step is performed by a step selected from the group consisting of:
   (a) screwing together an internal threaded surface with an external threaded surface;
   (b) screwing together internal thread segments with external thread segments; and
   c) engaging a substantially uniform surface with a substantially frustum surface.

23. The method of claim 21, wherein said matching surfaces are selected from the group consisting of:
   (a) a second outer surface and a matching third outer surface;
   (b) a first outer surface and a matching inner surface;
   (c) matching threaded surfaces; and
   (d) a substantially uniform surface and a matching substantially frustum surface.

24. The method of claim 21, wherein the placing step includes inserting the floss into at least one notch.

25. The method of claim 21, wherein the placing step is performed by extending the floss substantially from one side of said one member over said surface of said one member to substantially the other side of said one member, whereby the floss may be held against both sides of said one member to facilitate the retention of the floss.

26. A method of fastening a dental floss, comprising the steps of:
   retaining the floss on a surface of one of a first member and a second member, whereby the floss may extend substantially from one side of said one member to substantially the other side of said one member, whereby the floss may be held against both sides of said one member to facilitate the retention of the floss, the other of said first and second members having a matching surface thereon, said surfaces being engageable with each other to fasten the floss between said surfaces; and
   locking said first and second members together so that the floss is fastened between said surfaces, whereby said first and second members having the floss fastened therein are manipulated by a hand in lieu of winding the floss around a finger for teeth cleaning.

27. The method of claim 26, wherein the locking step is performed by a step selected from the group consisting of:
   (a) screwing together an internal threaded surface with an external threaded surface;
   (b) screwing together internal thread segments with external thread segments; and
   (c) engaging a substantially uniform surface with a substantially frustum surface.

28. The method of claim 26, wherein said matching surfaces are selected from the group consisting of:
   (a) a second outer surface and a matching third outer surface;
   (b) a first outer surface and a matching inner surface;
   (c) matching threaded surfaces; and
   (d) a substantially uniform surface and a matching substantially frustum surface.

29. The method of claim 26, wherein the retaining step includes inserting the floss into at least one notch.

30. A method of fastening a dental floss, comprising the steps of:
   placing the floss on one of a first member and a second member, said first member having a first outer surface thereon, said second member having an inner surface formed substantially at an inner end thereof, said surfaces being engageable with each other to fasten the floss between said surfaces; and
   locking said first and second members together so that the floss is fastened between said first outer surface and said inner surface, whereby said first and second members having the floss fastened therein are manipulated by a hand in lieu of winding the floss around a finger for teeth cleaning.

31. The method of claim 30, wherein the locking step is performed by a step selected from the group consisting of:
   (a) screwing together an internal threaded surface with an external threaded surface;
   (b) screwing together internal thread segments with external thread segments; and
   (c) engaging a substantially uniform surface with a substantially frustum surface.

32. The method of claim 30, wherein the placing step includes inserting the floss into at least one notch.

33. The method of claim 30, wherein the placing step is performed by extending the floss substantially from one side of said one member over said surface of said one member to substantially the other side of said one member, whereby the floss may be held against both sides of said one member to facilitate the retention of the floss.

34. The method of claim 30, wherein said first outer surface is formed substantially at an outer end of said first member.

* * * * *